United States Patent
Griffiths et al.

(10) Patent No.: US 6,555,721 B2
(45) Date of Patent: *Apr. 29, 2003

(54) PROCESS FOR THE PREPARATION OF MONO-OLEFINS FROM PARAFFINIC HYDROCARBONS

(75) Inventors: David Charles Griffiths, Esher (GB); Barry Martin Maunders, Woking (GB); William Terence Woodfin, Hook (GB)

(73) Assignee: BP Chemicals Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 10/093,725

(22) Filed: Mar. 11, 2002

(65) Prior Publication Data

US 2002/0143220 A1 Oct. 3, 2002

Related U.S. Application Data

(63) Continuation of application No. 09/632,633, filed on Aug. 4, 2000, now Pat. No. 6,395,944, which is a continuation of application No. PCT/GB99/02955, filed on Sep. 7, 1999.

(30) Foreign Application Priority Data

Sep. 10, 1998 (GB) .............................................. 9819645

(51) Int. Cl.$^7$ .............................. C07C 1/00; C07C 4/02; C07C 5/327

(52) U.S. Cl. ........................ 585/324; 585/648; 585/653; 585/658

(58) Field of Search .................................. 585/324, 648, 585/653, 658

(56) References Cited

U.S. PATENT DOCUMENTS

| | | | |
|---|---|---|---|
| 3,652,454 A | 3/1972 | Robin et al. ................. | 252/373 |
| 4,264,435 A | 4/1981 | Read, Jr. et al. ............. | 208/127 |
| 4,849,575 A | 7/1989 | Lewis ......................... | 585/642 |
| 5,382,741 A | 1/1995 | Astbury et al. .............. | 585/652 |

FOREIGN PATENT DOCUMENTS

| | | |
|---|---|---|
| DE | 195 07 098 A1 | 9/1996 |
| EP | 178853 | 10/1984 |
| EP | 0 199 475 A1 | 10/1986 |
| EP | 0 332 289 B1 | 3/1995 |
| GB | 794157 | 4/1958 |

*Primary Examiner*—Thuan D. Dang
(74) *Attorney, Agent, or Firm*—Nixon & Vanderhye

(57) ABSTRACT

Process for producing a mono-olefin from a feedstock containing a paraffinic hydrocarbon comprising feeding a gaseous paraffinic hydrocarbon-containing feedstock and a molecular oxygen-containing gas to an autothermal cracker wherein they are reacted in the presence of a catalyst capable of supporting combustion beyond the normal fuel rich limit of flammability to produce a product comprising one or more mono-olefin(s) and synthesis gas, and wherein the autothermal cracker is operated at a temperature greater than 650° C. and at a pressure of greater than 5 bar absolute. The product is separated into a high pressure fuel gas stream comprising methane, carbon monoxide and hydrogen and a stream comprising one or more olefins and recovering the one or more olefin(s). The high pressure fuel gas stream comprising methane, carbon monoxide and hydrogen separated in the second step is passed to a Fischer-Tropsch reactor containing a Fischer-Tropsch catalyst, wherein the stream is converted to hydrocarbons and wherein the Fischer-Tropsch is operated at a pressure of between 5–50bar absolute. Thereafter at least part of the hydrocarbon product is recovered.

7 Claims, 2 Drawing Sheets

PROCESS FOR THE PREPARATION OF MONO-OLEFINS FROM PARAFFINIC HYDROCARBONS

This application is a continuation of 09/632,633 filed Aug. 4, 2000 now U.S. Pat. No. 6,395,944 which is a continuation of PCT/GB99/02955 filed Sep. 7, 1999.

The present invention relates in general to the production of mono-olefins by the oxidative dehydrogenation of gaseous paraffinic hydrocarbons having two or more carbon atoms and in particular to the production of mono-olefins by autothermal cracking, especially of ethane, propane, and butanes.

BACKGROUND OF THE INVENTION

A known commercial route to the production of olefins is via steam cracking of paraffinic hydrocarbons. Steam cracking involves pyrolysis of the hydrocarbons. Olefins can also be prepared by cracking a paraffinic feed wherein the heat required for pyrolysis is provided by the partial combustion of the feedstock and not by conventional tubular fired heaters as in steam cracking. This process can be described as "autothermal cracking" and will be described as such hereinafter. Autothermal cracking may be accomplished in the absence of a catalyst, as described for example, an article entitled "Autothermal Cracking for Ethylene Production" by R. M. Deanesly in Petrol. Refiner, 29 (September, 1950), 217 and GB-A-794,157, or in the presence of a catalyst capable of supporting combustion beyond the normal fuel rich limit of flammability as described in, for example, EP-A-0164864; EP-A-0178853; EP-B1-0332289; EP-B1-0529793, and EP-A-0709446.

EP-A-0164864 and EP-A-0178853 describe the production of olefins together with carbon monoxide and hydrogen from gaseous paraffinic hydrocarbons, including ethane, by partial oxidation in spouted or fluid bed reactors. EP-A-0178853, for example, discloses a process for the preparation of synthesis gas (carbon monoxide and hydrogen) from a hydrocarbon feed wherein the saturated hydrocarbon and an oxygen-containing gas are introduced in a ratio of 1.1 to 5 times the stoichiometric ratio of hydrocarbon to oxygen for complete combustion. This process does not require a catalyst for its operation.

EP-B1-0332289 provides a process for the production of a mono-olefin from a gaseous paraffinic hydrocarbon having at least two carbon atoms or a mixture thereof by partially combusting a mixture of the hydrocarbon(s) and a molecular oxygen-containing gas in a composition of from 5 to 9 times the stoichiometric ratio of hydrocarbon to molecular oxygen-containing gas for complete combustion to carbon dioxide and water, in contact with a catalyst capable of supporting combustion beyond the normal fuel rich limit of flammability.

EP-B1-0529793 discloses a process for the production of mono-olefins from a paraffin-containing hydrocarbon feed having at least two carbon atoms, the process comprising (A) a first step of partially combusting a mixture of the hydrocarbon feed and a molecular oxygen-containing gas in contact with a catalyst capable of supporting combustion beyond the normal fuel rich limits of flammability, said first step carried out under a total pressure of greater than 5 bar absolute and at a temperature of greater than 650° C., and (B) a second step of cooling the mono-olefinic products to 600° C. or less within less than 50 milliseconds of formation.

Finally, EP-A-0709446 discloses a process for the conversion of a liquid paraffin-containing hydrocarbon which comprises the steps of:

(a) partially combusting a mixture of the liquid hydrocarbon and a molecular oxygen-containing gas in a reaction chamber with a catalyst capable of supporting combustion beyond the normal fuel rich limit of flammability, the mixture having a stoichiometric ratio of hydrocarbon to oxygen of greater than the stoichiometric ratio required for complete combustion to carbon dioxide and water, to produce a product stream and a carbon deposit in the reaction chamber, (b) periodically replacing the liquid hydrocarbon and molecular oxygen-containing gas mixture in step (a) with a fuel-rich carbon-containing stream for a period of time sufficient to effect substantial removal of the carbon deposit from the reaction chamber.

In addition to the valuable olefinic product(s) the autothermal cracking reaction produces both carbon monoxide and hydrogen, which in admixture is hereinafter to be referred to as "synthesis gas". The resulting synthesis gas from autothermal cracking is usually used as a fuel. This is a problem because it represents a waste of a valuable resource and therefore imposes an economic penalty on the process. A solution to this problem is to recover the synthesis gas and convert it to higher value products.

SUMMARY OF THE INVENTION

Accordingly, the present invention provides a process for the production of a mono-olefin from a feedstock comprising a paraffinic hydrocarbon which process comprises the steps of:

(a) feeding the feedstock and a molecular oxygen-containing gas to an autothermal cracker, where they are reacted by oxidative dehydrogenation to form a product comprising one or more mono-olefin(s) and synthesis gas, (b) separating the product from step (a) into a synthesis gas-containing stream and one or more olefins and recovering the one or more olefin(s), (c) contacting synthesis gas-containing stream separated in step (b) with either:

(i) a catalyst for the conversion of synthesis gas to methanol under conditions whereby synthesis gas is converted to methanol, and optionally thereafter or simultaneously contacting the methanol so-formed with a catalyst for the dehydration of methanol to ethylene, under conditions whereby methanol is converted to ethylene and recovering the ethylene, or optionally methanol or both; or (ii) a catalyst for the water gas shift reaction under conditions whereby carbon monoxide in the synthesis gas is converted by reaction with water to hydrogen and carbon dioxide and thereafter recovering hydrogen; or (iii) a catalyst for the conversion of synthesis gas to hydrocarbons under conditions whereby synthesis gas is converted to a hydrocarbon product and thereafter recovering at least a part of the hydrocarbon product.

The term "oxidative dehydrogenation" is not intended to be limiting in any way and broadly describes the chemistry involved. It is believed that both partial oxidation and cracking occur in the reaction.

The feedstock may be oxidatively dehydrogenated in the autothermal cracker in the presence or absence of a catalyst capable of supporting combustion beyond the normal fuel rich limit of flammability, preferably in the presence of such a catalyst. The principal role of the catalyst is to stabilise partial combustion of the gaseous mixture which may not otherwise be flammable. Suitably the catalyst is a supported platinum group metal. Preferably, the metal is either platinum or palladium, or a mixture thereof. Although a wide range of support materials are available, it is preferred to use alumina as the support. The support material may be in the form of spheres, other granular shapes or ceramic foams. Preferably, the foam is a monolith which is a continuous multichannel ceramic structure, frequently of a honeycomb appearance. A preferred support for the catalytically active metals is a gamma alumina. The support is loaded with a mixture of platinum and palladium by conventional methods well known to those skilled in the art. The resulting compound is then heat treated to 1200° C. before use. Catalyst promoters may also be loaded onto the support. Suitable promoters include copper and tin.

The catalyst may be used as a fixed bed or as a solids recirculating bed, for example a fluid or spouted bed. Use of the catalyst in a fixed bed can avoid the problem of attrition, which is mainly associated with moving bed operations. Moreover, the use of a fixed bed also facilitates rapid quenching of the products as compared with the use of a fluid bed.

In the process for the production of a mono-olefin from a feedstock comprising a gaseous paraffinic hydrocarbon the paraffinic hydrocarbon may suitably be ethane, propane or butane. The paraffinic hydrocarbon may be substantially pure or may be in admixture with other hydrocarbons and optionally other materials, for example methane, nitrogen, carbon monoxide, carbon dioxide, steam or hydrogen. A paraffinic hydrocarbon-containing fraction such as naphtha, gas oil, vacuum gas oil, or mixtures thereof, may be employed. A suitable feedstock is a mixture of gaseous paraffinic hydrocarbons, principally comprising ethane, resulting from the separation of methane from natural gas. A preferred feedstock is a paraffinic hydrocarbon principally comprising ethane which provides a product principally comprising ethylene as the mono-olefin.

As the molecular oxygen-containing gas there may suitably be used either oxygen or air. It is preferred to use oxygen, optionally diluted with an inert gas, for example nitrogen. It is preferred to pre-mix the oxygen-containing gas and the paraffinic hydrocarbons feedstock prior to contact with the catalyst, when present. In the presence of a catalyst the composition of the gaseous paraffinic hydrocarbon/molecular oxygen-containing gas mixture is suitably from 5 to 13.5 times the stoichiometric ratio of hydrocarbon to oxygen-containing gas for complete combustion to carbon dioxide and water. The preferred composition is from 5 to 9 times the stoichiometric ratio of hydrocarbon to oxygen-containing gas.

The autothermal cracker may suitably be operated at a temperature greater than 500° C., for example greater than 650° C., typically greater than 750° C., and preferably greater than 800° C. The upper temperature limit may suitably be up to 1200° C., for example up to 1100° C., preferably up to 1000° C.

It is preferred, although not essential, to preheat the feedstock and the oxygen-containing gas to suitably 200 to 500° C., preferably 200–300° C.

The autothermnal cracker may be operated at atmospheric or elevated pressure. Pressures of 1 to 30 bara may be suitable, preferably a pressure of 1.1 bara to 5 bara, for example, 1.8 bara is employed. However, a total pressure of greater than 5 bar absolute can also be suitably employed.

Preferably, the gaseous feedstock and the molecular oxygen-containing gas are fed to the autothermal cracker in admixture under a Gas Hourly Space Velocity (GHSV) of greater than 80,000 hr$^{-1}$ in order to minimise the formation of carbon monoxide and carbon dioxide. Preferably, the GHSV exceeds 200,000 hr $^{-1}$, especially greater than 1,000,000 hr$^{-1}$. For the purposes of the present invention GHSV is defined as:

vol. of total feed at NTP/Time/(vol. of catalyst bed).

For further details of preferred methods of operation reference may be made to the aforesaid EP-B1-0332289; EP-B1-0529793; and EP-A-0709446.

In addition to mono-olefins and synthesis gas, small amounts of acetylenes, aromatics and carbon dioxide are generally co-produced.

In step (b) of the process of the invention the product from step (a) of the process is separated into synthesis gas-containing stream and one or more mono-olefin(s) and the one or more mono-olefin(s) are recovered. Means for separating synthesis gas from mono-olefins are well-known in the art In step (c) of the process of the invention synthesis gas-containing stream separated in step (b) is contacted in alternative (i) with a catalyst for the conversion of synthesis gas to methanol under conditions whereby synthesis gas is converted to methanol and optionally thereafter, or simultaneously, the methanol so-formed is contacted with a catalyst for the dehydration of methanol to ethylene under conditions whereby methanol is converted to ethylene and the ethylene, or optionally the methanol, or both, is recovered.

In alternative (ii) of step (c) of the process synthesis gas-containing stream separated in step (b) is contacted with a catalyst for the water gas shift reaction whereby carbon monoxide in the synthesis gas is converted by reaction with water to hydrogen and carbon dioxide and thereafter hydrogen is recovered. The water gas shift reaction may be represented as:

$$CO+H_2O \rightleftharpoons CO_2+H_2 \tag{I}$$

The water gas shift reaction is well-known in the art. It is generally operated in the presence of a catalyst. Typically an iron oxide catalyst may be employed, although other catalysts know in the art may be employed. Temperatures typically in the range from 350 to 500° C. may suitably be used. Conditions known in the art for driving the equilibrium towards the formation of hydrogen are preferably employed.

The water reactant may be some or all of the water produced as a by-product in the oxidative dehydrogenation of the paraffinic hydrocarbon. Additionally further water may be added if desired.

In alternative (iii) of step (c) of the process of the invention synthesis gas-containing stream separated in step (b) is contacted with a catalyst for the conversion of synthesis gas to hydrocarbons under conditions whereby synthesis gas is converted to a hydrocarbon product, and thereafter at least a part of the hydrocarbon product is recovered.

The conversion of synthesis gas into hydrocarbons has been known for many years, it being generally known as the Fischer-Tropsch (FT) process. The process produces hydrocarbons from $C_1$ upwards, but principally in the $C_5$–$C_{60}$ range. In recent years attention has been directed to the FT process as one of the more attractive direct and environmentally acceptable routes to high quality transportation fuels from alternative energy sources such as coal and natural gas via intermediate formation of synthesis gas.

Thus, there may be recovered from the FT product a desirable hydrocarbon fraction boiling in the diesel range There may also be recovered a less valuable fraction of lower boiling point, which fraction is generally referred to as naphtha. Not all of this fraction is industrially utiliseable. In a preferred embodiment the recovered naphtha fraction is recycled at least in part as feedstock to the autothermal cracker in the process of the present invention. This leads to the advantage that the FT process and the process for the production of a mono-olefin by the oxidative dehydrogenation of a gaseous paraffinic hydrocarbon complement each other in the respect that the synthesis gas by-product of the oxidative dehydrogenation is usefull as feed to the FT process and the lesser value naphtha product of the FT process is useful as a feedstock in the oxidative dehydrogenation. Moreover, a significant additional advantage is that the high pressure "fuel gas" stream comprising methane, carbon monoxide and hydrogen obtained from the conventional autothermal cracking separation via a demethaniser in step (II) may be used directly as feedstock to the FT reactor in step (III) wherein the carbon monoxide/hydrogen component is consumed leaving methane and residual carbon monoxide as a more conventional fuel gas. Thus, the FT reactor functions as a reactor/separator adding value to the carbon monoxide/hydrogen and eliminating a separation stage.

Accordingly, in a preferred embodiment the present invention provides an integrated process for the production of a mono-olefin and a hydrocarbon fraction boiling in the diesel range which process comprises the steps of:

(I) feeding a gaseous paraffinic hydrocarbon-containing feedstock and a molecular oxygen-containing gas to an autothermal cracker wherein they are reacted in the presence or absence of a catalyst capable of supporting combustion beyond the normal fuel rich limit of flammability under conditions whereby the feedstock is oxidatively dehydrogenated to a product comprising one or more mono-olefin(s) and synthesis gas, (II) separating the product from step (I) into synthesis gas and one or more mono-olefin(s) and recovering the one or more mono-olefin(s), (III) feeding synthesis gas separated in step (II), optionally together with additional synthesis gas, to an FT reactor containing an FT catalyst wherein the synthesis gas is reacted under FT conditions to produce an FT product comprising naphtha and hydrocarbons boiling in the diesel range, (IV) separating the FT product from step (III) into a naphtha fraction and a diesel range hydrocarbon fraction and recovering the diesel range hydrocarbon fraction, and (V) preferably recycling the naphtha fraction recovered in step (IV) as feed to the autothermal cracker of step (I).

Steps (I) and (II) of the preferred embodiment have been described hereinbefore.

As regards step (III) the catalyst may suitably comprise at least one metal selected from cobalt, nickel, iron, molybdenum, tungsten, thorium, ruthenium, rhenium, and platinum. Of the aforesaid metals cobalt, nickel and iron are preferred. Generally, the metals may be used in combination with a support material. Suitable support materials include alumina, silica and carbon, and mixtures of two or more thereof. The use of cobalt, for example, as a catalytically active metal in combination with a support is well-known from, for example EP-A-127220; EP-142887;GB-A-2146350; GB-A-2130113; EP-A-0209980;EP-A-0261870 and GB-A-2125062. Of these EP-A-127220, for example, discloses the use of a catalyst comprising (i) 3–60 pbw cobalt, (ii) 0.1–100 pbw zirconium, titanium, ruthenium or chromium, per 100 pbw silica, alumina or silica-alumina, (iii) the catalyst having been prepared by kneading and/or impregnation. EP-A-0209980 describes the use in the conversion of synthesis gas to hydrocarbons of a catalyst having a composition represented by the formula:

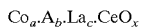

wherein

A is an alkali metal a is greater than zero and up to 25% w/w, b is in the range from zero to 5% w/w, c is in the range from zero to 15% w/w, x is a number such that the valence requirements of the other elements for oxygen is satisfied, and the remainder of the composition, subject to the requirement for x, is cerium.

EP-A-0261870 discloses a composition for use after reductive activation as a catalyst in the conversion of synthesis gas to hydrocarbons, which composition comprises as essential components (i) cobalt either as the elemental metal, the oxide or a compound thermally decomposable to the elemental metal and/or oxide and (ii) zinc in the form of the oxide or a compound thermally decomposable to the oxide.

Any of the aforesaid catalysts may be used in the process of the present invention and for further details of the catalysts their preparation and use reference may be made to the publications.

FT conditions are suitably a temperature in the range from 160 to 350° C., preferably from 180 to 275° C., and a pressure in the range from 0 to 100 bar, preferably from 5 to 50 bar. The GHSV for continuous operation may suitably be in the range from 100 to 25000 h$^{-1}$.

The process of step (III) may be carried out batchwise or continuously, preferably continuously, in a fixed bed, fluidised bed or slurry phase reactor.

The additional synthesis gas is suitably obtained by the partial oxidation of a carbonaceous substance, e.g. coal or by catalytic partial oxidation of methane, or liquified petroleum gases. Preferably, the synthesis gas is obtained by the catalytic steam reforming of methanes either as such or in the form of natural gas. Steam reforming and catalysts therefor are well-known in the art. Typically, a supported nickel catalyst is employed. The carbon monoxide to hydrogen ratio of the synthesis gas may suitably be in the range from 2:1 to 1:6, preferably from 2:1 to 1:2. Whilst the ratio of carbon monoxide to hydrogen in the synthesis gas produced by the aforesaid processes may differ from these ranges, it may be altered appropriately by the addition of either component, or may be adjusted by the shift reaction as mentioned hereinbefore.

In step (IV) of the preferred embodiment the FT product from step (III) is separated into a naphtha fraction and a diesel range hydrocarbon fraction. This separation may be accomplished by any of the means known in the art. Generally, the fractions may be separated by distillation. Preferably, the diesel range hydrocarbon produced in step (IV) is highly paraffinic, with good combustion characteristics. Preferably also, the diesel range hydrocarbon substantially no metal, nitrogen, sulfur or aromatic impurities. If such impurities are present however, their concentrations are kept to a minimum. For example, the sulphur content of the diesel fraction may be less than 0.01 wt %, and more preferably less than 0.001% weight. The diesel range hydrocarbon may have a density of 0.7 to 0.9 g/ml., preferably, 0.8 g/ml. Its pour point may be between −35 to −45° C., preferably about −38 to −40° C.

In step (V) the naphtha fraction recovered in step (IV) is preferably recycled as feed to the autothermal cracker of step (I) Alternatively some, or all, the naphtha fraction may be recovered, and used elsewhere.

BRIEF DESCRIPTION OF THE DRAWINGS

A preferred embodiment of the invention will now be further described by reference to the accompanying drawings, in which.

DETAILED DESCRIPTION OF PREFERRED EMBODIMENTS

Figure 1:
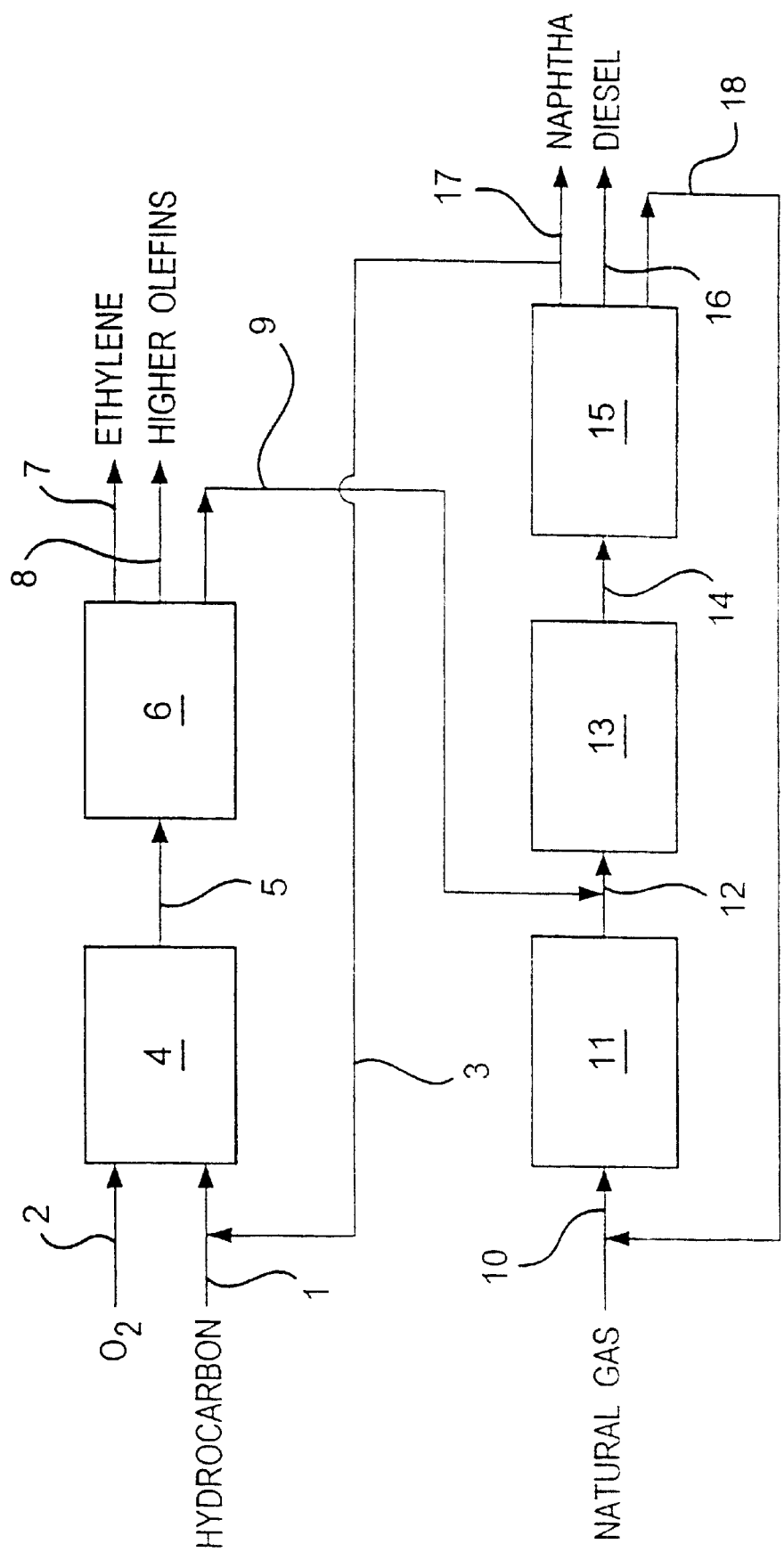
FIG. 1 is a simplified flow sheet showing a first embodiment of the present invention in operation.

Reference is first made to FIG. 1 of the drawings, which depicts a first embodiment of the present invention.

A paraffinic hydrocarbon feedstock, principally comprising ethane, is fed through line 1 to the autothermal cracker 4. Also fed to the autothermal cracker through line 2 is oxygen. The autothermal cracker 4 is maintained under conditions whereby oxidative dehydrogenation is effected to produce ethylene, higher olefins, methane, carbon dioxide, and synthesis gas (carbon monoxide and hydrogen). The product is passed through line 5 to a product separation zone 6 wherein a mixture of synthesis gas and methane is separated cryogenically from ethylene and higher olefins The ethylene and higher olefins are removed from the separation zone, for example, via lines 7 and 8.

The mixture of synthesis gas and methane recovered from the product separation zone 6 is fed through line 9 to the FT reactor 13. Also fed to the reactor 13 through line 12 is synthesis gas produced by the steam reformer 11 to which is fed natural gas through line 10. In the FT reactor 13 synthesis gas is converted to hydrocarbons which are passed through line 14 to the product separation zone 15 in which (i) methane is separated and recycled through line 18 as feed to the reformer 11, (ii) hydrocarbons boiling in the diesel range are separated and recovered through line 16 and (iii) naphtha is separated and removed through line 17. At least a part of the naphtha is recycled through line 3 as feed to the autothermal cracker 4.

Figure 2:
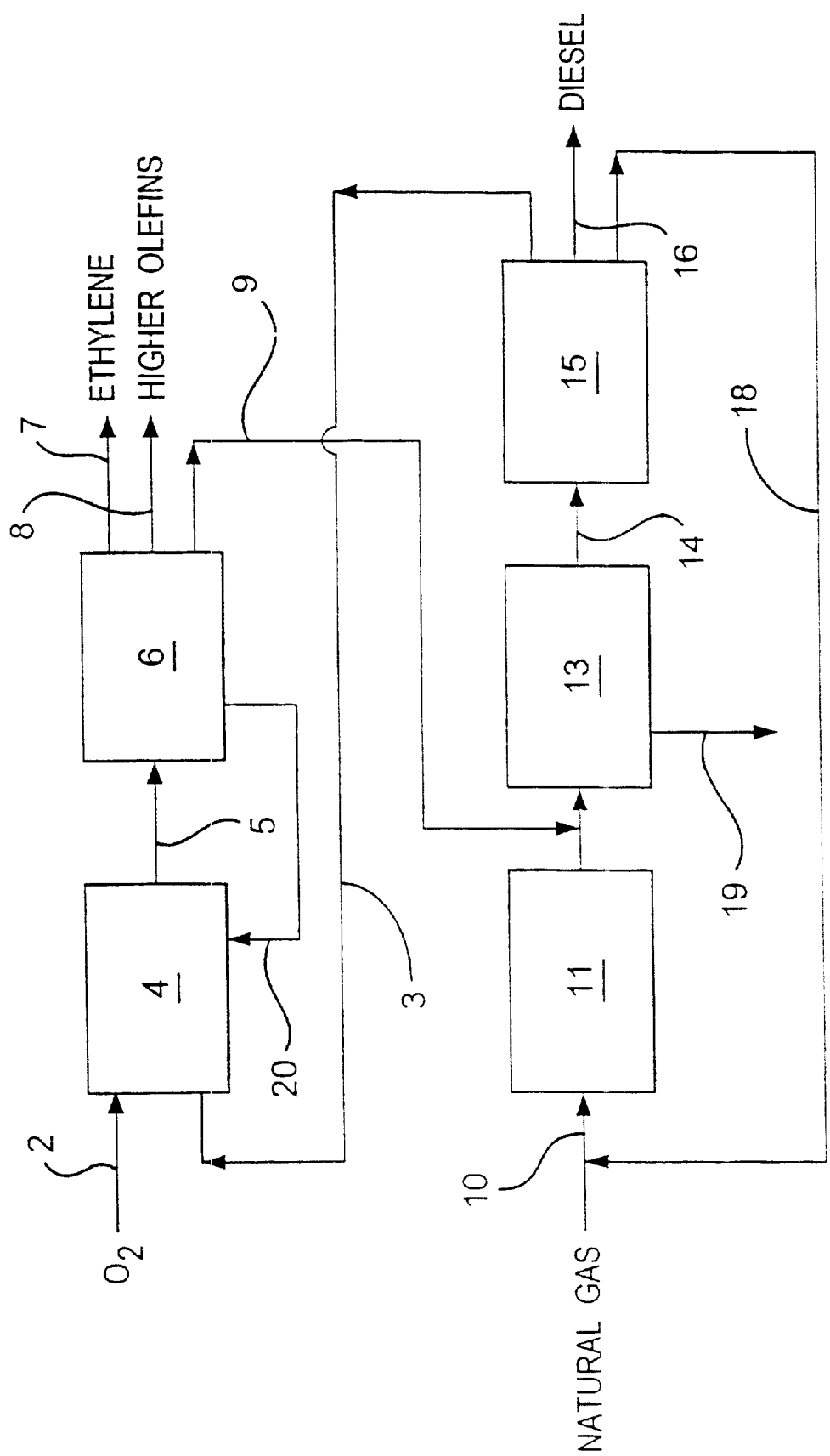
FIG. 2 is a simplified flow sheet showing a second embodiment of the present invention in operation.

Reference is now made to FIG. 2 of the drawings, which depicts an alternative embodiment to the embodiment depicted in FIG. 1. Like parts are referred to with like numerals.

With reference to FIG. 2, oxygen is fed through line 2 to the autothermal cracker 4. Also fed to the autothermal cracker is recycled naphtha, which enters the cracker 4 via line 3 Unlike the embodiment of FIG. 1, a paraffinic hydrocarbon feedstock is not introduced into the cracker via line 1. The autothermal cracker 4 is maintained under conditions whereby oxidative dehydrogenation is effected to produce ethylene, higher olefins, methane, carbon dioxide, and synthesis gas (carbon monoxide and hydrogen) The product is passed through line 5 to a product separation zone 6 wherein a mixture of synthesis gas and methane is separated cryogenically from ethylene and higher olefins. The ethylene and higher olefins are removed from the separation zone, for example, via lines 7 and 8.

The mixture of synthesis gas and methane recovered from the product separation zone 6 is fed through line 9 to the FT reactor 13. Also fed to the reactor 13 is synthesis gas produced by the steam reformer 11 to which is fed natural gas through line 10. In the FT reactor 13, synthesis gas is converted to hydrocarbons which are passed to the product separation zone 15 in which (i) methane is separated and recycled through line 18 as feed to the reformer 11, (ii) hydrocarbons boiling in the diesel range are separated and recovered through line 16 and (iii) naphtha is recycled through line 3 as feed to the autothermal cracker 4. Unlike, the embodiment of FIG. 1, all the naphtha produced in the FT reactor 13 is recycled. Water produced in the FT reactor 13 is removed through line 19. The hydrocarbon stream recovered through line 16 was analysed and found to be extremely paraffinic. The steam contained no metals, nitrogen, sulfur or aromatics, and had quality combustion characteristics. Table 1 below summarises the density, sulphur content and cetane number of the diesel produced:

TABLE 1

| density | 0.79 g/ml |
|---|---|
| pour point | −39 C. |
| cetane number | 75 |
| sulfur content | <0.001% weight |

The flow rates through lines 2, 3, 5, 7 to 10, and 16 and 19 are tabulated below

TABLE 2

| Line Number | Flow rate (TE/hr) |
|---|---|
| 2 | 85 |
| 3 | 200 |
| 5 | 304 |
| 7 | 83.4 |
| 8 | 20.8 |
| 9 | 105 |
| 10 | 908 |
| 16 | 466 |
| 19 | 467 |

What is claimed is:

1. A process for the production of a mono-olefin from a feedstock comprising a paraffinic hydrocarbon which process comprises the steps of:

(a) feeding a gaseous paraffinic hydrocarbon-containing feedstock and a molecular oxygen-containing gas to an autothermal cracker wherein they are reacted in the presence of a catalyst capable of supporting combustion beyond the normal fuel rich limit of flammability to produce a product comprising one or more mono-olefin(s) and synthesis gas and wherein the autothermal cracker is operated at a temperature greater than 650° C. and at a pressure of greater than 5 bar absolute, (b) separating the product from step (a) into a high pressure fuel gas stream comprising methane, carbon monoxide and hydrogen and a stream comprising one or more olefins and recovering the one or more olefin (s), (c) passing the high pressure fuel gas stream comprising methane, carbon monoxide and hydrogen separated in step (b) to a Fischer-Tropsch reactor containing a Fischer-Tropsch catalyst wherein said stream is converted to hydrocarbons, and thereafter recovering at least a part of the hydrocarbon product and wherein the Fischer-Tropsch reactor is operated at a pressure of between 5–50 bar absolute.

2. A process according to claim 1 wherein the hydrocarbon product comprises a hydrocarbon fraction boiling in the diesel range, and/or a hydrocarbon fraction boiling in the naphtha range.

3. A process according to claim 1 wherein the high pressure fuel gas stream comprising methane, carbon monoxide and hydrogen separated in step (b) is fed directly to the Fischer-Tropsch reactor.

4. A process according to claim 1 wherein part of the hydrocarbon product produced is recovered, and part of the hydrocarbon product is recycled to the autothermal cracker as the feedstock.

5. A process as claimed in claim 4 wherein hydrocarbon boiling in the naphtha range is recycled at least in part as feedstock to the autothermal cracker.

6. A process as claimed in claim 1 wherein the Fischer-Tropsch reaction is carried out continuously using a reactor selected from the group consisting of a fixed bed reactor, fluidized bed reactor and a slurry phase reactor.

7. A process as according to claim 1 wherein the carbon monoxide to hydrogen ratio of the high pressure fuel gas stream employed is 2:1 to 1:6.

* * * * *